United States Patent [19]

Felix

[11] 4,054,667

[45] Oct. 18, 1977

[54] CERTAIN 4-CYCLOPROPYLPHENYL GERANYL ETHERS AND THEIR USE IN CONTROLLING INSECTS

[75] Inventor: Raymond A. Felix, El Cerrito, Calif.

[73] Assignee: Stauffer Chemical Company, Westport, Conn.

[21] Appl. No.: 658,782

[22] Filed: Feb. 17, 1976

[51] Int. Cl.$^2$ .................... A01N 9/28; C07D 303/00
[52] U.S. Cl. ................... 424/278; 260/612 D; 260/613 D; 424/340; 424/341; 424/DIG. 12; 542/413
[58] Field of Search ....... 424/278, 340, 341, DIG. 12; 260/240 H, 240 R, 612 D, 613 D

[56] References Cited

U.S. PATENT DOCUMENTS

| | | | |
|---|---|---|---|
| 3,825,602 | 7/1974 | Pallos et al. | 260/609 R |
| 3,950,328 | 4/1976 | Karrer | 260/240 H |

OTHER PUBLICATIONS

Annual review of Biochemistry, vol. 40, 1096–1097 (1971).

*Primary Examiner*—Leonard Schenkman
*Attorney, Agent, or Firm*—Edith A. Rice

[57] ABSTRACT

Compounds which are useful for controlling insects by impeding their metamorphosis, have the formula

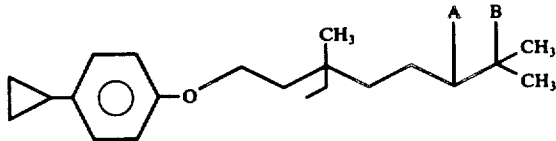

wherein i. A and B together form a bond,
  ii. A and B together form an epoxide link,
or
  iii. A is hydrogen and B is $C_1$-$C_4$ alkoxy.

8 Claims, No Drawings

CERTAIN 4-CYCLOPROPYLPHENYL GERANYL ETHERS AND THEIR USE IN CONTROLLING INSECTS

BACKGROUND OF THE INVENTION

This invention relates to certain novel 4-cyclopropylphenyl geranyl ethers and to their use as insect hormones to control insect populations.

There is a class of compounds which acts in a different manner on insects than presently used insecticides and exerts a disrupting influence upon the normal development of insects. Such compounds impede the normal pupation of insects and result in the formation of members of the treated species which are non-viable or sterile. This ultimately leads, indirectly at least, to the destruction of the insect population.

Compounds of this type are believed to have further advantages in that they are non-toxic to warm-blooded animals and highly effective in controlling insects at low dosages. It is also hoped that it will be more difficult for insects to develop resistance to these compounds. Compounds of this type are described in U.S. Pat. Nos. 3,766,208, 3,851,061, 3,410,894, 3,914,321 and others.

DETAILED DESCRIPTION OF THE INVENTION

The compounds of the present invention that are useful in controlling insects have the general structural formula

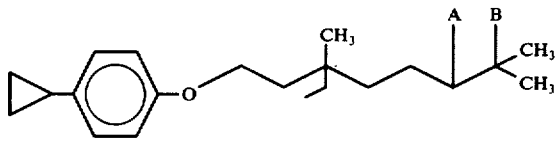

wherein
i. A and B together form a bond,
ii. A and B together form an epoxide link,
or
iii. A is hydrogen and B is $C_1$-$C_4$ alkoxy.

Carbon atoms joined to two or less hydrogen atoms occupy each angle in the backbone of the compound represented by the above formula unless otherwise specified.

The compounds of the present invention can be prepared by reacting 4-cyclopropylphenol with the appropriate geranyl halide compound. The reaction can be represented as follows

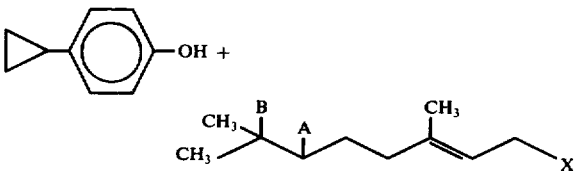

wherein X is chlorine, bromine or iodine and A and B are as defined above. Preferably, the reaction is carried out in a solvent such as acetone, with stirring while slowly adding an acid acceptor, such as potassium carbonate, at room temperature followed by heating at reflux to complete the reaction. The reaction product is recovered by conventional techniques, for example extracting the residue with a solvent, such as methylene dichloride, followed by drying over anhydrous magnesium sulfate and removing the solvent be evaporation.

EXAMPLE I

This example illustrates the preparation of the intermediate 4-cyclopropylphenol.

In a 500 ml three-necked flask equipped with a reflux condenser, magnetic stirring bar and addition funnel were placed 103.8 g (0.6 mole) p-bromophenol, 150 mg p-toluene sulfonic acid as catalyst and 200 ml ehtyl ether. The reaction mixture was cooled to 5° C and 60 g (0.7 mole) of dihydropyran was added with stirring. When the addition was complete the reaction mixture was allowed to come to room temperature and then stirred 24 hours. The ether solution was then washed with 100 ml 1 M NaOH and separated. The ether layer was dried over anhydrous magnesium sulfate and evaporated to yield 143 g (93%) of 2-(4-bromophenoxy)-tetrahydropyran, an amber oil.

In a 3000 ml three-necked flask equipped with a reflux condenser, mechanical stirrer and an addition funnel were placed 29 g (1.21 mole) of magnesium turnings which were then flamed out under a nitrogen flow. To this was added 500 ml of dry tetrahydrofuran under a nitrogen atmosphere and the reaction initiated by the addition of iodine and 1,2-dibromoethane, as evidenced by the disappearance of the iodine color. Then 291 g (1.1 mole) of 2-(4-bromophenoxy)-tetrahydropyran was added at a rate to sustain the reflux of the solvent. When the addition was over the mixture was refluxed 3 hours. The mixture was then cooled with an ice bath and 1 g of the catalyst dichloro-[1,2-bis(diphenylphosphino)ethane] nickel (II) was added followed by the portionwise addition of 150 g (1.4 mole) of vinyl bromide at 5° C. The reaction mixture was stirred overnight. Then 500 ml of water was added along with 1000 ml of ether. The layers were separated. The organic layer was then dried over anhydrous magnesium sulfate and evaporated to yield 250 g of an amber oil. The residue was distilled at 0.1 mm to yield 144 g of 2-(4-vinylphenoxy)-tetrahydropyran, bp 95°-105° C.

In a 250 ml three-necked flask equipped with a magnetic stirring bar, reflux condenser, and addition funnel were placed 20.4 g (0.1 mole) of 2-(4-vinylphenoxy)-tetrahydropyran, 51 g (0.2 mole) bromoform and 2 g benzyl triethylammonium chloride as catalyst. The reaction mixture was stirred and 40 g (0.5 mole) of 50% sodium hydroxide was added dropwise. The reaction mixture was stirred at 35° C for 4 hours. Water was added and the mixture extracted with methylene dichloride. The organic layer was dried over anhydrous magnesium sulfate and the solvent evaporated. Excess bromoform was removed at 45° C under a 0.1 mm vacuum. A yield of 36 g of 2[4-(1,1-dibromocyclopropylphenoxy)] tetrahydropyran, a dark amber oil, was obtained.

In a 500 ml flask equipped with a reflux condenser and magnetic stirring bar were placed 36 g (0.1 mole) of 2-[4-(1,1-dibromocyclopropylphenoxy)] tetrahydropyran, 150 ml of acetic acid and 20 ml water. The solution was stirred for 72 hours at room temperature. Most of the acetic acid was removed by evaporation and the residue dissolved in 250 ml of ether. The ether solution was washed three times with equal volumes of water. The ether solution was then washed with dilute caustic until the washings were basic. The water layer was then acidified with hydrochloric acid and extracted with methylene dichloride. The methylene dichloride layer was dried over anhydrous magnesium sulfate and the solvent evaporated. A yield of 11 g of 4-(1,1-dibromocyclopropyl) phenol, a dark oil, was obtained.

In a 500 ml flask equipped with a reflux condenser, and magnetic stirring bar under a nitrogen atmosphere were placed 11 g (37.6 moles) of dibromocyclopropylphenol, 100 ml of toluene, and 50 g of 70% solution of "Red-Al" [sodium bis(2-methoxyethoxy aluminum hydride)] in benzene. The solution was then heated to reflux for 6 hours and allowed to stir overnight at room temperature. The reaction was then quenched with water and acidified with concentrated hydrochloric acid. The layers were separated and the aqueous layer extracted with 100 ml of ether. The organic layers were combined and washed with dilute base. The water layer was then acidified with concentrated hydrochloric acid and extracted with methylene dichloride. The methylene dichloride extract was dried over anhydrous magnesium sulfate and the solvent evaporated. A yield of 3 g of 4-cyclopropylphenol, an amber oil, was obtained.

EXAMPLE II

This example illustrates the preparation of 4-cyclopropylphenyl geranyl ether.

In a 50 ml flask equipped with a reflux condenser and magnetic stirring bar were placed 800 mg (6 m moles) 4-cyclopropylphenol, 900 mg (5.2 m moles) geranyl chloride, 1 g (7.25 m moles) potassium carbonate and 10 ml acetone. The mixture was heated to reflux with stirring for 11 hours. Then 100 ml water was added and the mixture was extracted with pentane. The pentane layer was dried over anhydrous magnesium sulfate and the solvent evaporated. A yield of 740 mg of residue having $N_D^{30} = 1.5072$ was obtained.

EXAMPLE III

This example illustrates the preparation of 4-cyclopropylphenyl geranyl ether epoxide.

In a 50 ml flask equipped with a reflux condenser and magnetic stirring bar were placed 1.6 g (12 m moles) 4-cyclopropylphenol, 2.1 g (11 m moles) geranyl chloride epoxide, 2.1 g (15 m moles) potassium carbonate and 10 ml acetone. The solution was then heated to reflux with stirring for 4 hours and allowed to stir overnight at room temperature. Then 100 ml of water was added and the mixture extracted with methylene dichloride. The methylene dichloride layer was dried over anhydrous magnesium sulfate and the solvent evaporated. A yield of 2 g of a thick oil residue was obtained. The structure of the product was confirmed by IR.

EXAMPLE IV

This example illustrates the preparation of 4-cyclopropylphenyl (3,7-dimethyl-7-ethoxyocta-2-enyl)ether.

In a 50 ml flask equipped with a reflux condenser and magnetic stirring bar were placed 1.2 g (9 m moles) 4-cyclopropylphenol, 1.9 g (8.7 m moles) of 1-chloro-3,7-diemthyl-7-ethoxy-2-octene, 1.4 g (10 m moles) potassium carbonate and 10 ml acetone. The mixture was heated to reflux with stirring for 5 hours. Then 100 ml of water was added and the solution extracted with pentane. The pentane layer was dried over anhydrous magnesium sulfate and evaporated. A yield of 2.2 g of residue having $N_D^{30}$ 1.4810 was obtained.

INSECTICIDE EVALUATION TEST

The degree of activity of a test compound to hinder or impede the metamorphosis of insects is measured by treating the larval or pupal stage of a representative insect with the compound and examining it after its last molt toward the adult form for retention of immature features. The compounds of the present invention were tested by the following procedures. The results are shown in Table I.

Golden Mealworm (*Tenebrio molitor*). Test compounds are diluted in acetone and topically applied in 1 μl drops to the abdomen of mealworm pupae which are less than 24 hours old. Treated pupae are incubated for seven days at 28° C, after which observations are made on the emerged adults. Abnormalities include the retention of urogomphi, gin traps, pupal cuticle, or adult-larval intermediates. Test concentrations range from 10 μg per pupa down to that at which approximately 50% of the emerged adults are abnormal.

Southern House Mosquito [*Culex pipiens quinquefasciatus* (Say)]. Insect growth regulator activity is determined using late fourth-instar larvea of the mosquito *Culex pipiens quinquefasciatus*. Ten larvae are placed in a six ounce, number 67 Dixie wax paper cup containing 100 ml of an aqueous solution of the test chemical. The cups are covered with black tulle cloth and stored at 70° F for approximately 1 week. During this week the larvae in the inactive and/or control cups will pupate and emerge as adult mosquitoes. Larvae in cups containing active compounds will usually pupate and either die before the adult emerges or the adult will begin to emerge but die in the process. Test concentrations range from 1 PPM down to that at which approximately 50% of the adults are able to successfully emerge.

Housefly (*Musca domestica* L.). Test chemicals are diluted in acetone and topically applied in 1 μl drops to pre-pupal housefly larvae. Treated larvae are placed in 55 × 17 mm glass Petri dishes with a 55 mm filter paper disk in the bottom. They are then covered with a thin layer of slightly moist soil and stored at 80° F until all control larvae have pupated and emerged as adults. Active compounds prevent the emergence of adults from the pupal cases. Test rates range from 1 μg/larva down to that at which 50% of the flies emerge normally.

| Compound | *Tenebrio molitor* (μg/pupae) | *Culex pipiens quinquefasciatus* (PPM) | *Musca domestica* (μg/larva) |
|---|---|---|---|
| 1 | 1.0 | 0.2 | >1 |
| 2 | 0.1 | 0.0005 | >1 |
| 3 | 0.003 | 0.004 | >1 |

Compound 1—4-cyclopropylphenyl geranyl ether
Compound 2—4-cyclopropylphenyl geranyl ether eposide
Compound 3—4-cyclopropylphenyl(3,7-dimethyl-7-ethoxyocta-2-enyl) ether The compounds of this invention are generally embodied into a form suitable for convenient application. For example, the compounds can be embodied into pesticidal compositions which are provided in the form of emulsions, suspensions, solutions, dusts, and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays;

propellants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid compositions, for example, an emulsion, suspension, or aerosol spray. While the concentration of the active pesticide in the present compositions can vary within rather wide limits, ordinarily the pesticide compound will comprise not more than about 50% by weight of the composition. Preferably, however, the pesticide compositions of this invention will be in the form of solutions or suspensions containing about 0.1 to 1.0% weight of the active pesticide compound.

What is claimed is:

1. A compound having the general structural formula

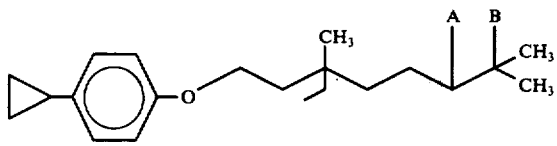

wherein
 i. A and B together form a bond,
 ii. A and B together form an epoxide link,
or
 iii. A is hydrogen and B is $C_1$-$C_4$ alkoxy.

2. The compound of claim 1 wherein A and B together form a bond.

3. The compound of claim 1 wherein A and B together form an epoxde link.

4. The compound of claim 1 wherein A is hydrogen and B is ethoxy.

5. A method of controlling insects selected from the group consisting of *Tenebrio molitor* and *Culex pipiens* comprising applying thereto at the larval or pupal stage an insecticidally effective amount of a compound having the formula

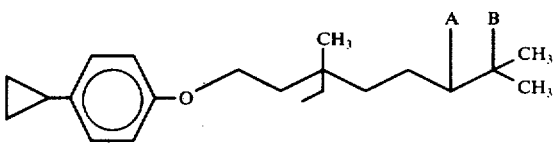

where
 i. A and B together form a bond,
 ii. A and B together form an epoxide link,
or
 iii. A is hydrogen and B is $C_1$-$C_4$ alkoxy.

6. The method of claim 5 wherein A and B together form a bond.

7. The method of claim 5 wherein A and B together form an epoxide link.

8. The method of claim 5 wherein A is hydrogen and B is ethoxy.

* * * * *